United States Patent [19]

Kurihara et al.

[11] Patent Number: 5,480,795
[45] Date of Patent: Jan. 2, 1996

[54] CURCULIN B AND DNA ENCODING SAME, AND PROCESS FOR PRODUCTION THEREOF

[75] Inventors: Yoshie Kurihara, 4-7, Okuzawa 7-chome, Setagaya-ku, Tokyo 116; Soichi Arai, 38, Nanashimacho, Kanagawa-Ku,Yokohama-shi, Kanagawa-ken 221; Keiko Abe, Warabi; Haruyuki Yamashita, Arakawa, all of Japan

[73] Assignees: Yoshie Kurihara, Tokyo; Soichi Arai, Yokohama; Asahi Denka Kogyo K.K., Tokyo, all of Japan

[21] Appl. No.: 845,592

[22] Filed: Mar. 4, 1992

[30] Foreign Application Priority Data

Mar. 4, 1991 [JP] Japan .................................... 3-061012

[51] Int. Cl.[6] .......................... C12N 15/29; C12P 19/34; C12P 21/02
[52] U.S. Cl. ........................ 435/91.4; 435/69.1; 435/91.1; 536/23.6
[58] Field of Search .......................... 530/379; 536/23.6; 435/69.1, 91.1, 91.4

[56] References Cited

U.S. PATENT DOCUMENTS

| | | | |
|---|---|---|---|
| 5,242,693 | 9/1993 | Kurihara et al. | 426/3 |
| 5,378,489 | 1/1995 | Kurihara et al. | 426/602 |
| 5,395,921 | 3/1995 | Kurihara | 530/350 |
| 5,405,641 | 4/1995 | Kurihara et al. | 426/655 |

FOREIGN PATENT DOCUMENTS 0139501  5/1985  European Pat. Off. .
0351566  1/1990  European Pat. Off. .

OTHER PUBLICATIONS

Abe, K. et al.; Biochem. Biophys. Acta 1130:232–234 (1992).
Kurihara, Crit. Rev. Food Sci. Nutrition 32:231–252 (1992).
Yamashita, et al., Journal of Biological Chemistry, Sep. 1990, vol. 265, No. 26, pp. 15770–15775.
Edens, et al., Trends in Biotechnology, 1985, vol. 3, No. 3, pp. 61–64.
Sambrook, J. et al., Molecular Cloning, 1989, pp. 8.46–8.52.

*Primary Examiner*—Robert A. Wax
*Assistant Examiner*—Eric Grimes
*Attorney, Agent, or Firm*—Sherman and Shalloway

[57] ABSTRACT

Essentially pure curculin B is disclosed. A process for producing curculin B, includes the steps of: culturing a transformed cell or microorganism containing a recombinant DNA containing a base sequence encoding curculin B, whereby curculin B is produced by the transformed cell or microorganism, and isolating curculin B from the transformed cell or microorganism. A DNA encoding mature or premature curculin B is also disclosed. DNA including a base sequence encoding curculin B, is produced by: separating a fraction containing a curculin B mRNA from *Curculigo latifolia*, preparing a single-stranded DNA from the mRNA using reverse transcriptase, preparing a double-stranded DNA from the single-stranded DNA, inserting the double-stranded DNA into a vector, transforming a host with the vector to produce a cDNA library, and isolating a cDNA encoding curculin B from the library, using one or more synthesized DNA's containing a base sequence coding for a partial amino acid sequence elucidated from curculin A purified from *Curculigo latifolia*, as a probe.

9 Claims, 6 Drawing Sheets

AATTCGGCAGAG
    GCCGTGCTC p

1

CURCULIN B AND DNA ENCODING SAME, AND PROCESS FOR PRODUCTION THEREOF

BACKGROUND OF THE INVENTION

1. Field of the Invention

The present invention relates to curculin B and a DNA encoding the same, and a process for production thereof.

2. Description of the Related Art

*Curculigo latifolia* is a plant belonging to Hypoxidaceae (or Amaryllidaceae according to a different method of classification) and grows naturally in Western Malaysia, the southern part of Thailand, etc. Curculin homologue (hereinafter referred to as curculin), the protein contained in *Curculigo latifolia*, has been recognized by the inventors of the present invention in the past as being useful as a taste-modifier. Further, the inventors described curculin obtained from *Curculigo latifolia* in Japanese Unexamined Published Patent Application (Kokai) No. 2-104263 and disclosed a method of stabilization of curculin in Japanese Unexamined Published Patent Application (Kokai) No. 2-84157 and methods of processing curculin in Japanese Unexamined Published Patent Application (Kokai) No. 2-84160 and Japanese Unexamined Published Patent Application (Kokai) No. 2-84161. Further, the complete amino acid sequence of a curculin (hereinafter referred to as curculin A) in curculin homologue is described in Japanese Unexamined Published Patent Application (Kokai) No. 3-190899.

However, in the techniques described in said Japanese Unexamined Published Patent Applications (Kokai) No. 2-104263, No. 2-84157, No. 2-84160, No. 2-84161 and No. 3-190899, the curculin was extracted from the *Curculigo lacifolia* plant, and so mass production was difficult. Further, there were the problems that the *Curculigo latifolia* plant is not easily handled, and further the activity of the curculin obtained by the extraction method is likely to be lowered.

SUMMARY OF THE INVENTION

The present inventors, with the aim of providing a means for mass production of curculin, prepared oligonucleotides using the already elucidated amino acid sequence of curculin A, and used the oligonucleotide as a probe to succeed in cloning the cDNA encoding another curculin (hereinafter referred to as curculin B), a curculin homologue. Further, the fact was confirmed that the microorganisms transformed by a plasmid containing the above cloning DNA produced curculin B, and thus the invention was completed.

Therefore, the present invention relates to essentially pure curculin B. In the present specification, the "essentially pure curculin B" particularly means curculin B essentially free of other proteins of *Curculigo latifolia* origin, and may be produced by recombinant host cells or microorganisms in accordance with the present invention.

2

The present invention also relates to a DNA including a base sequence encoding curculin B.

Further, the present invention relates to a process for producing curculin B, comprising: culturing a transformed cell or microorganism containing a recombinant DNA containing a base sequence encoding curculin B, whereby curculin B is produced by the transformed cell or microorganism, and isolating curculin B from the transformed cell or microorganism.

Still further, the present invention relates to a process for producing a DNA including a base sequence encoding curculin B, comprising: separating a fraction containing a curculin B mRNA from *Curculigo latifolia*, preparing a single-stranded DNA from the mRNA using reverse transcriptase, preparing a double-stranded DNA from the single-stranded DNA, inserting the double-stranded DNA into a vector, transforming a host with the vector to produce a cDNA library, and isolating a cDNA encoding curculin B from the library, using one or more synthesized DNA's containing a base sequence coding for a partial amino acid sequence elucidated using curculin A purified from *Curculigo latifolia*, as a probe.

DESCRIPTION OF THE PREFERRED EMBODIMENTS

Figures 1, 2:
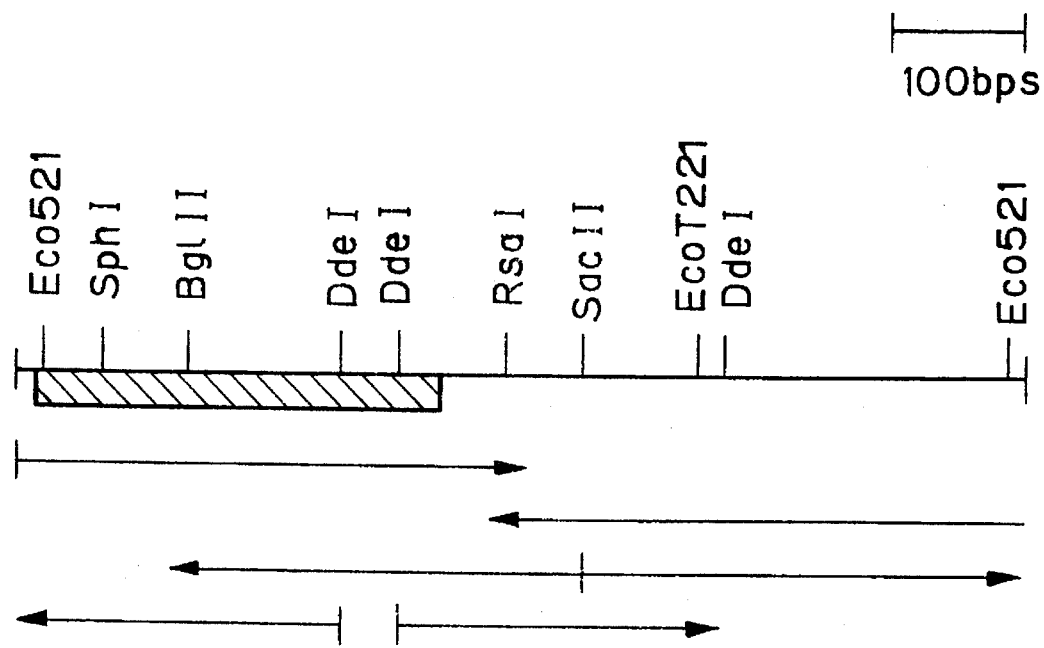
FIG. 1 illustrates the structure of an EcoRI adapter.
FIG. 2 is a restriction map of the cloning DNA encoding curculin B.

It is assumed that curculin is produced in the plant cells in the form of a premature protein including a prepeptide or a prepropeptide, and the mature protein is formed by separating the prepeptide or prepropeptide in processing. According to the discovery of the present inventors, the mature curculin B is comprised of 114 amino acids having an amino acid sequence of the formula (I):

| Asp | Asn | Val | Leu | Leu | Ser | Gly | Gln | Thr | Leu | His | Ala | Asp | His | Ser |
| --- | --- | --- | --- | --- | --- | --- | --- | --- | --- | --- | --- | --- | --- | --- |
| Leu | Gln | Ala | Gly | Ala | Tyr | Thr | Leu | Thr | Ile | Gln | Asn | Lys | Cys | Asn |
| Leu | Val | Lys | Tyr | Gln | Asn | Gly | Arg | Gln | Ile | Trp | Ala | Ser | Asn | Thr |
| Asp | Arg | Arg | Gly | Ser | Gly | Cys | Arg | Leu | Thr | Leu | Leu | Ser | Asp | Gly |
| Asn | Leu | Val | Ile | Tyr | Asp | His | Asn | Asn | Asn | Asp | Val | Trp | Gly | Ser |
| Ala | Cys | Trp | Gly | Asp | Asn | Gly | Lys | Tyr | Ala | Leu | Val | Leu | Gln | Lys |
| Asp | Gly | Arg | Phe | Val | Ile | Tyr | Gly | Pro | Val | Leu | Trp | Ser | Leu | Gly |

| | | | | | | | | | |
|---|---|---|---|---|---|---|---|---|---|
| Pro | Asn | Gly | Cys | Arg | Arg | Val | Asn | Gly | SEQ ID NO: 1 |

Further, the premature curculin B is comprised of the 158 amino acids having an amino acid sequence of the formula (II):

| | | | | | | | | | | | | | | |
|---|---|---|---|---|---|---|---|---|---|---|---|---|---|---|
| Met | Ala | Ala | Lys | Phe | Leu | Leu | Thr | Ile | Leu | Val | Thr | Phe | Ala | Ala |
| Val | Ala | Ser | Leu | Gly | Met | Ala | Asp | Asn | Val | Leu | Leu | Ser | Gly | Gln |
| Thr | Leu | His | Ala | Asp | His | Ser | Leu | Gln | Ala | Gly | Ala | Tyr | Thr | Leu |
| Thr | Ile | Gln | Asn | Lys | Cys | Asn | Leu | Val | Lys | Tyr | Gln | Asn | Gly | Arg |
| Gln | Ile | Trp | Ala | Ser | Asn | Thr | Asp | Arg | Arg | Gly | Ser | Gly | Cys | Arg |
| Leu | Thr | Leu | Leu | Ser | Asp | Gly | Asn | Leu | Val | Ile | Tyr | Asp | His | Asn |
| Asn | Asn | Asp | Val | Trp | Gly | Ser | Ala | Cys | Trp | Gly | Asp | Asn | Gly | Lys |
| Tyr | Ala | Leu | Val | Leu | Gln | Lys | Asp | Gly | Arg | Phe | Val | Ile | Tyr | Gly |
| Pro | Val | Leu | Trp | Ser | Leu | Gly | Pro | Asn | Gly | Cys | Arg | Arg | Val | Asn |
| Gly | Gly | Ile | Thr | Val | Ala | Lys | Asp | Ser | Thr | Glu | Pro | Gln | His | Glu |
| Asp | Ile | Lys | Met | Val | Ile | Asn | Asn | SEQ ID NO: 2 | | | | | | |

Therefore, the present invention also relates to a DNA characterized by including a base sequence encoding the mature or premature curculin B having the amino acid sequence of the formula (I) or (II), and further to a DNA containing a base sequence comprising the said base sequence containing ATG (coding for the starting methionine) bonded therewith, for the production of the mature or premature curculin B by microorganisms or culture cells.

It is possible to change one or more parts of the structure of the DNA or the structure of the corresponding peptide without changing the main activity, by natural or artificial mutation. Therefore, the above-mentioned DNA's of the present invention include even DNA's containing base sequences encoding polypeptides having the structures corresponding to homologous mutants of all of the above-mentioned polypeptides.

The DNA encoding curculin B can be obtained by the following method.

(A) Extraction of mRNA

Fruit of the *Curculigo lactifolia*, which produces curculin in particularly high concentration, was pulverized, and the RNA was extracted from a sample of the powder. The RNA can be extracted using the guanidine-thiocyanate method (Maniatis et al.: Molecular Cloning, A Laboratory Manual, Cold Spring Harbor Laboratory, New York (1982)) or the phenol-SDS method (Brawerman et al., *Biochemistry*, 11, 637-641 (1972)).

The guanidine-thiocyanate method comprises adding a guanidine-thiocyanate solution to the sample, then homogenizing the same. The homogenate obtained is placed in a swing rotor polyallomer tube and centrifuged to obtain the RNA residue. The RNA residue is refined to obtain the mRNA.

The phenol-SDS method comprises adding a tris-hydrochloride buffer solution containing phenol, EDTA and SDS, and dithiothreitol to the powder sample to obtain an aqueous phase. The resulting aqueous phase contains substances other than RNA, such as polysaccharides, so lithium chloride etc. is used for a salting-out procedure so as to obtain the RNA residue. Then, the RNA residue is redissolved in a suitable solvent and the mRNA is extracted by purifying with an oligo (dT) column (Aviv et al., *Proc. Natl. Acad. Sci. U.S.A.* 69, 1408-1418 (1972)). In the present invention, it is preferable to use the phenol-SDS method, because the plant of *Curculigo latifolai* or the like has a hard cell membrane.

(B) Synthesis of cDNA and Insertion of cDNA in Vector

For the synthesis of the cDNA, the method of Okayama-Berg (Okayama et al.: *Mol. Cell Biol.* 2, 161 (1982)), the method of Gubler-Hoffman (Gubler et al.: *Gene* 25, 263 (1983)), or the like may be used.

The Okayama-Berg method will be explained hereinafter.

[1] A pBR322-SV40 vector plasmid is cleaved by the restriction enzyme KpnI, then oligo dT is added. Further, the restriction enzyme HpaI is reacted. Then, an oligo dA cellulose (Pharmacia LKB Biotechnology Co.) column is used to remove the products without additional dT or with a short oligo dT chain, thereby preparing the vector primer.

[2] Another pBR322-SV40 fused plasmid DNA is cleaved by the restriction enzyme PstI and purified. Then, an oligo dG chain is attached to prepare a linker DNA having a base sequence which may be cleaved by the restriction enzyme HindIII.

[3] The purified mRNA and the vector primer prepared in the above item [1] are mixed, and reverse transcriptase is used to synthesize the cDNA.

[4] An oligo dG chain is attached to the primer which fused with the synthesized cDNA, then HindIII was used for digestion, and the portion with the attached oligo dG chain at the opposite side to the end where the cDNA was fused is removed.

[5] The linker DNA with the oligo dG chain prepared by the above item [2] and the vector primer-DNA-mRNA hybrid prepared in the above item [4] are formed into a ring by ligating the HindIII fragments using T4 ligase or another DNA ligase, then the RNA is partially digested by ribonuclease H. Then, the RNA fragment is used as a primer and the RNA chain is replaced with the DNA chain by DNA polymerase. T4 ligase was used for ligating DNA's to prepare a double-stranded DNA.

[6] The competent cells are prepared, then transformation is performed and the cells are incubated in a medium containing ampicillin (for example, χ-broth, LB-broth, or YT-broth) so as to obtain colonies containing the desired DNA.

An explanation will be made of the Gubler-Hoffman method. In this method, it is possible to use λgt10, λgt11, λZAP, or the like as the vector.

[1] Oligo dT annealed to the poly A portion of the purified mRNA is used as the primer, and reverse transcriptase is used to synthesize the first strand cDNA (or sscDNA).

[2] Ribonuclease H or another endo-type RNase is added to the cDNA-mRNA hybrid prepared in the above item [1] to digest the mRNA, then dATP, dTTP, dGTP, and dCTP are added, a reaction is caused with DNA polymerase I or Klenow fragments etc. to synthesize the second strand cDNA (or dscDNA).

[3] The dscDNA prepared by the above item [2] is treated by a T4 DNA polymerase reaction to make its two ends uniform and the EcoRI site is methylated by EcoRI methylase, then an EcoRI linker is attached to the two ends and EcoRI digestion is performed.

[4] The EcoRI digested cDNA prepared by the above item [3] and EcoRI digested λgt vector are ligated by T4 ligase, then packaged to prepare a library.

The synthesis of the cDNA and the insertion of the cDNA in the vector may be performed in the above way. In the present invention, however, as shown in the later-mentioned examples, it is preferable to use the Gubler-Hoffman method and it is preferable to use λgt10 as the vector.

(C) Preparation of Probes

Curculin A has already been purified from the *Curculigo latifolia* plant by the present inventors. The complete amino acid sequence of the protein was determined, and disclosed in Japanese Unexamined Published Patent Application (Kokai) No. 3-190899. Suitable portions of the amino acid sequence may be selected to prepare the probes. The synthesis of the DNA used as the probes may be performed using a known method (for example, the phosphoamidite method using an automatic DNA synthesizer, The Japanese Biochemical Society ed., Genetic Research Methods I, 1-27 (1986) or Matteucci et al., *Tetrahedron Lett.*, 21, 719 (1980)).

(D) Screening

Screening of the plaques containing the desired gene from the cDNA library prepared in the above item (B) may be performed using the probes prepared in the above item (C). The plaques are baked on a nylon membrane or nitrocellulose or other filter membranes. Then, the probes obtained in the above item (C) are labeled by radioactive isotopes such as [$^{32}$P] by a method described in the aforementioned reference of Manitis et al. etc. The plaques baked on the above filter membranes and the probes labeled by $^{32}$P etc. are hybridized to carry out the screening of the plaques including the desired gene.

Further, for the screening of the plaques containing the desired gene from the cDNA library, the method described in Glover, DNA Cloning, 1, 51–52, IRL Press may also be used. The screening method comprises detecting the activity of the protein corresponding to an expression of the desired cDNA, or detecting the protein corresponding to an expression of the desired cDNA using an antibody specific to the protein, and identifying the cDNA. However, in the present invention, the method using plaque hybridization (or colony hybridization) is desirable.

(E) Subcloning

The examples of the vector which may be used for the subcloning are plasmids of the pUC line (for example, pUC7, pUC8, pUC9, pUC18, or pUC19) or the pBR line (for example, pBR322, pBR325, or pBR327). In particular, it is preferable to use pUC18. Phage DNA or plasmid DNA is extracted and purified from the plaques or colonies selected by the above-mentioned screening process and is digested by a suitable restriction enzyme and inserted into a subcloning vector.

The thus obtained recombinant vector is introduced into the competent cells by the method described, for example, in Hanahan et al., *Mol. Biol.* 166, 557–580 (1983). As the host cells, there may be mentioned, cells derived from *E. coli* K12 strain, such as HB101 or MM294, MC1061, C600, DH1, and JM109. The thus obtained transformant may be determined by, for example, the method described in the above-mentioned reference of Maniatis et al., for example, the method using isopropyl-β-D-thiogalactopyranoside (IPTG).

(F) Preparation of Plasmid DNA

It is possible to purify plasmid DNA from the clones obtained by subcloning by, for example, the alkali-SDS method described in the above-mentioned reference of Maniatis et al or the Boiling method. If necessary, the cesium chloride ultracentrifugation method may also be used.

(G) Structural Analysis of cDNA

The plasmid DNA obtained in the above item (F) is cleaved by various types of restriction enzymes to prepare a restriction map. Further, the dideoxy method (Sanger et al., *J. Mol. Biol.* 143, 161–178 (1980)) etc. are used to determine the nucleotide sequence.

(H) Expression

The plasmid DNA obtained in the above item (F) may be utilized and, for example, the method described in the above-mentioned reference of Maniatis et al. may be used so as to transform the competent cells of the *E. coli* YA21 strain to express curculin B. As the host cells for the expression, there may be mentioned *E. coli* MM294, DH1, DH5, JM109, HB101, GC508, or CES201 in addition to the above-mentioned *E. coli* YA21.

Further, as the vector which may be used in the present invention, there may be mentioned ColE1 plasmid vectors, such as the pUC line (for example, pUC7, pUC8, pUC9, pUC18, pUC19), the pBR line (for example, pBR322, pBR325 and pBR327), and further, their derivant pTV118, pUC118, pUC119, etc. Further, as the phage vectors, there may be mentioned the vectors derived from λ-phage, such as λgt10, λgt11, Charon 4A, λgtWES-λB, EMBL3, EMBL4, etc.

Further, as vectors for expression in yeast, there may be mentioned, for example, pYES2.0, pAH9, pMAC561, pLG669, pMA91, pAM82, pMC2010, pOP, pTE432, and pSD922. As vectors for expression in *Bacillus subtilis*, there may be mentioned, for example, pPL608, pKTH50, pKTH51, pKTH53, pKTH38, pHY300, pLH, etc. Also, as vectors for expression in the animal cells (for example, COS-7 cells, Bowes melanoma cells, CHO cells), there may be mentioned, for example, pMT, pSV, pCD, pMDSG, pBPV, etc.

The obtained transformant is incubated in a suitable known medium until the cell density reaches a sufficient concentration. Then, the cells are destroyed by, for example, ultrasonication, and the resulting liquid may be treated by a known method to purify curculin B. The obtained curculin B may be used as taste-modifiers, food, pharmaceuticals, and the like.

EXAMPLES

The present invention now will be further illustrated by, but is by no means limited to, the following Examples.

Example 1

Extraction of RNA

About 6 g of the fruit of *Curculigo latifolia* (a mixture of different fruit of different stages from shortly after flowering to full ripening, namely 0 week to about 8 weeks; all fruit components such as the fruit skin, seeds, pulp, and the like were included because of the use of the fruit as a whole) was frozen by dry ice and pulverized, while preventing from thawing, to obtain 5 g of powder.

To 5 g of resulting powder, 15 ml of phenol, 15 ml of 0.1M tris-hydrochloride buffer solution (pH 8.5, 5 mM-EDTA, 1% SDS), and 600 µl of 1M dithiothreitol were added. The mixture was immediately vigorously shaken. The aqueous phase was separated by centrifugation, and then extracted with phenol three times. The resulting aqueous phase included substances other than RNA such as polysaccharides. Therefore, 1.05 volumes of 5M lithium chloride was added, and the mixture was allowed to stand at 4° C. for 2 hours, then centrifuged to obtain the RNA as precipitate. Subsequently, the precipitate was treated with ethanol to obtain 768 µg of RNA.

Example 2

Extraction of mRNA

After 768 µg of RNA obtained in Example 1 was thermally denatured (65° C. for 10 minutes), and a 0.5M sodium chloride solution containing the thermally denatured RNA was prepared, the solution was passed through an oligo (dT) column (mRNA purifying column; Pharmacia LKB Biotechnology Co.). The unabsorbed fraction was removed by the 0.5M sodium chloride solution, and the column was eluted by an elution solution not containing sodium chloride so as to obtain 8 µg of the RNA in a high concentration.

Example 3

Synthesis of cDNA

A commercially available cDNA synthesis kit (cDNA Synthesis Kit; Pharmacia LKB Biotechnology Co.) was used to synthesize sscDNA from the mRNA and then dscDNA. The blunt ends were formed by Klenow fragments, and the EcoRI adapter was annealed.

Namely, to a buffer (first strand reaction mix) including oligo d(T) 12-18 primer, a reverse transcriptase of the Maloney's mouse leukemia virus (MMLV), dATP, dCTP, dGTP, and dTTP was added 20 µl of an RNase free water containing 4 µg of thermally denatured mRNA. The mixture was reacted at 37° C. for one hour. Then, to a buffer (second-strand reaction mix) containing RNase H, DNA polymerase I, dATP, dCTP, dGTP, and dTTP was added the above-mentioned reaction mixture to make the overall volume 100 µl. The whole was reacted at 12° C. for one hour and then at 22° C. for one hour. After the reaction was completed, 1 µl of Klenow fragments was added, and the mixture was reacted at 37° C. for 30 minutes. One hundred µl of phenol/chloroform was added, then the mixture was centrifuged for one minute and the upper aqueous phase was purified by a column. To 100 µl of the eluate were added 4 µl of an EcoRI adapter (structure shown in FIG. 1) solution, 1 µl of an ATP solution, and 3 µl of T4 DNA ligase. The mixture was gently agitated and centrifuged for a short time, then was reacted at 12° C. over night. The reaction solution was heated at 65° C. for 10 minutes to denature the DNA ligase and was cooled with ice, then 10 µl of an ATP solution and 1 µl of T4 polynucleotidekinase were added. The mixture was gently agitated, then reacted at 37° C. for 30 minutes. To the reaction solution was added 100 µl of phenol/chloroform, then the mixture was centrifuged for one minute, the upper aqueous phase was purified by a column, and thus an EcoRI adapter-ligated dscDNA was obtained.

Example 4

Insertion of cDNA into Vector

The EcoRI site of λgt10 was cleaved by EcoRI, treated by alkali phosphatase and then dephosphorylated, and the EcoRI adapter-ligated dscDNA obtained in Example 3 was ligated thereto.

To find the best mixture ratio, test ligation was performed. Namely, 2 µl of λgt10, 3 µl of 3M sodium acetate and 60 µl of cold ethanol were added to 30 µl of the eluate obtained in Example 3 (diluted by a column buffer solution to obtain solutions containing 5.0 ng, 15.0 ng, or 40.0 ng of dscDNA). The whole was mixed, cooled at −70° C. for 15 minutes, and then centrifuged for 10 minutes to obtain the precipitate. The resulting precipitate was dried. The dried cDNA was resuspended in 9 µl of a column buffer solution, then 1 µl of an ATP solution and 1 µl of T4 DNA ligase were added. After agitation, the mixture was centrifuged, and reacted at 12° C. for 16 hours. Then, according to the method described in the above-mentioned reference of Maniatis et al, the in-vitro-packaging (Giga pack gold) was carried out, and *E. coli* c600hfl was infected with the recombinant phage, whereupon it was found that the best results were obtained when 0.3 µg of λgt10 was mixed with 40 ng of EcoRI adapter-ligated dscDNA. Then, the ligation and the packaging were scaled up using the above molar ratio to prepare a library comprised of about 300,000 independent plaques.

Example 5

Screening

Based on the amino acid sequence of the curculin A described in Japanese Unexamined Published Patent Application (Kokai) No. 3-190899, the following three types of probes were prepared. In the following base sequence, N indicates the deoxyribonucleic acid residues of A, C, G and T, H indicates A, C and T, D indicates A, G and T, R indicates A and G, K indicates G and T, and Y indicates C and T. As the synthesis method, the method described in the above-mentioned reference of The Japanese Biochemical Society (Genetic Research Methods I) was employed.

(1) Sense DNA probe based on Ile-Gln-Asn-Asn-Cys-Asn (25th to 30th amino acids from the amino end of the mature curculin A) (17 mer; 48 types);

5'-ATH-CAR-AAK-AAK-TGY-AA-3'(SEQ. ID NO:6)

(2) Antisense DNA probe based on Tyr-Gln-Asn-Gly-Arg-Gln-Ile-Trp-Ala (34th to 42nd amino acids) (26 mer, 1536 types):

5'-GC-CCA-DAT-YTG-NCK-NCC-RTT-YTG-RTA-3'(SEQ ID NO:7)

(3) Antisense DNA probe based on Phe-Val-Ile-Tyr-Gly-Pro-Val (94th to 100th amino acids) (20 mer; 768 types);

5'-AC-NGG-NCC-RTA-DAT-NAC-RAA-3'(SEQ ID NO:8)

These probes were labeled at the 5' ends with [λ-$^{32}$P] dATP, using T4 polynucleotidekinase, and then employed in the following Example 6.

Example 6

Plaque Hybridization

The plaques of the library obtained in Example 4 were transferred to a nylon membrane and the DNA's were fixed. Then, hybridization was carried out in order by the probes (1) to (3) prepared in Example 5. The temperature of the hybridization was 33° to 34° C. for the probe (1), 55° C. for the probe (2), and 45° to 46° C. for the probe (3). The washing conditions were 6×SSC (1×SSC being 0.15M sodium chloride and 0.015M sodium citrate) for each of the probes (1) to (3), while the temperatures were the same temperatures as the respective hybridization temperatures. As a result, 16 plaque groups hybridizing with all of the probes were obtained from the approximately 300,000 plaques.

Example 7

Isolation of Single Plaques

Secondary screening was carried out on each of the 16 plaque groups obtained in Example 6. Namely, each of the plaque groups was separated into independent plaques, which were successively hybridized with the probes (1) to (3) in the same manner as in Example 6. One plaque which hybridized with all of the probes (1) to (3) was obtained from each of the 16 plaque groups, respectively. The resulting plaques were named the phages λQ1 to λQ16. From these phages λQ1 to λQ16, the phage DNA's were extracted, digested by EcoRI and compared in the insert molecular weight by electrophoresis, whereupon it was found that the insert included in the phage λQ9 was the longest (about 1.2 kbp).

Example 8

Subcloning

Using pUC18, the insert included in the phage λQ9 was subcloned. Namely, from the phage λQ9, 30 µg of DNA of the phage λQ9 was purified by the method described, for example, in The Japanese Biochemical Society ed., Cont. Biochemical Experiment Lectures I, Genetic Research Methods 2, 100 (1986) and digested by 100 units of EcoRI to obtain 400 ng of EcQRI fragments encoding the curculin. On the other hand, pUC18 (50 ng) was cleaved by EcoRI, then treated by alkali phosphatase and dephosphorylized. Then, 20 µl of a ligation buffer solution (66 mM tris-hydrochloride buffer solution containing 0.01 mM ATP, 6.6 mM magnesium chloride, and 10 mM dithiothreitol, pH 7.6) containing the above-mentioned 100 ng of the EcoRI fragments and 1.0 µl of T4 ligase was added thereto and the mixture was incubated at 12° C. for 16 hours for the ligation.

Subsequently, transformation was carried out by the method described in the above-mentioned reference of Hanahan et al. Namely, 5 µl of the above-mentioned buffer solution containing 100 ng of c-DNA-plasmid DNA was added to 210 µl of the competent cells of E. coli MM 294 prepared for transformation. The mixture was allowed to stand at 0° C. for 30 minutes and at 42° C. for 80 seconds, then was cooled by ice. Thereafter, 800 µl of SOC medium was added and the mixture was shaken at 37° C. for one hour. Further, the mixture was incubated by an χ-broth agar medium containing 50 µg/ml of ampicillin at 37° C. to obtain about 100 transformants per plate.

Example 9

Colony Hybridization

The replicas of the plates obtained in Example 8 were denatured and baked by ordinary methods to fix the DNA. The probe (2) prepared in the above-mentioned Example 5 was used for hybridization at 55° C., and washed by 6×SSC at the same temperature. Seventy-five positive clones were obtained.

Example 10

Plasmid DNA

Figure 3:
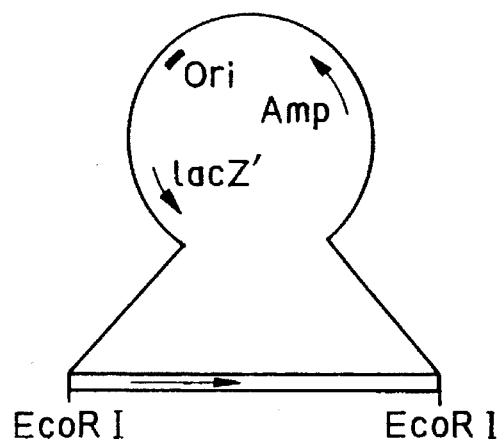
FIG. 3 illustrates the structure of plasmid pQ9.

One of the transformants considered positive in Example 9 was reimplanted in 30 ml of a χ-medium containing 50 µl/ml of ampillicin. The mixture was shaken and incubated at 37° C. over night, then centrifuged at 4° C. (7 minutes at 2000×g) to obtain about 200 µg of cells. The cells (approximately 200 µg were dissolved in 800 µl of a 25 mM tris-hydrochloride buffer solution (containing 50 mM glucose and 10 mM EDTA, pH 8.0) containing lysozyme (10 mg/ml). Then, about 20 µl of plasmid (hereinafter referred to as plasmid pQ9) DNA was obtained by the method described in the above-mentioned reference of Maniatis etal. The structure of the plasmid pQ9 is shown in FIG. 3 (in the insertion portion of FIG. 3, the arrow mark indicates the insertion direction of DNA encoding curculin B).

Example 11

Preparation of Restriction Map and Determination of Base Sequence

The plasmid pQ9 was cleaved by various restriction enzymes, and the restriction map shown in FIG. 2 was prepared. Further, the nucleotide sequences of the various DNA fragments were determined by the dideoxy method (see above-mentioned reference of Sanger et al.). The results are shown in the following Table 1. In the Table 1, the amino acid sequence deduced from the base sequence is also shown. The hatched portion in FIG. 2 shows the coding portion, while the arrow mark shows the direction of determination of the base sequence. Further, in the Table 1, each of the base sequences of the 5' and 3' nontranslational regions is one example, respectively. Namely, when the phage among λQ1 to λQ16 other than the phage λQ9 was used for the same treatment to determine the base sequence, sequences partially different from the base sequences of the 5' and 3' nontranslational regions shown in the Table 1 were found.

TABLE 1

| CGCAAAGACA | ATG | GCG | GCC | AAG | TTT | CTT | CTC | ACC | ATT | CTT | GTC | ACC |
|---|---|---|---|---|---|---|---|---|---|---|---|---|
|  | Met | Ala | Ala | Lys | Phe | Leu | Leu | Thr | Ile | Leu | Val | Thr |
|  | −20 |  |  |  |  |  | −15 |  |  |  |  |  |

TABLE 1-continued

```
TTT GCG GCC GTC GCT AGC CTT GGC ATG GCC GAC AAT GTC CTG CTC
Phe Ala Ala Val Ala Ser Leu Gly Met Ala Asp Asn Val Leu Leu
-10              -5              1                   5

TCC GGG CAA ACT CTG CAT GCC GAC CAC TCT CTC CAG GCG GGC GCC
Ser Gly Gln Thr Leu His Ala Asp His Ser Leu Gln Ala Gly Ala
                 10              15                  20

TAT ACC TTA ACC ATA CAA AAC AAG TGC AAC CTG GTG AAA TAC CAG
Tyr Thr Leu Thr Ile Gln Asn Lys Cys Asn Leu Val Lys Tyr Gln
                25              30                  35

AAC GGG AGG CAG ATC TGG GCT AGC AAC ACT GAC AGG CGG GGC TCC
Asn Gly Arg Gln Ile Trp Ala Ser Asn Thr Asp Arg Arg Gly Ser
                40              45                  50

GGC TGC CGC CTC ACA TTG CTG AGT GAC GGG AAC CTC GTT ATC TAC
Gly Cys Arg Leu Thr Leu Leu Ser Asp Gly Asn Leu Val Ile Tyr
                55              60                  65

GAC CAC AAC AAC AAC GAC GTG TGG GGG AGC GCC TGC TGG GGG GAC
Asp His Asn Asn Asn Asp Val Trp Gly Ser Ala Cys Trp Gly Asp
                70              75                  80

AAC GGC AAG TAT GCT CTT GTT CTT CAG AAG GAT GGC AGA TTT GTC
Asn Gly Lys Tyr Ala Leu Val Leu Gln Lys Asp Gly Arg Phe Val
                85              90                  95

ATC TAT GGC CCG GTT TTG TGG TCC CTT GGC CCT AAT GGG TGC CGC
Ile Tyr Gly Pro Val Leu Trp Ser Leu Gly Pro Asn Gly Cys Arg
                100             105                 110

CGT GTT AAT GGT GGA ATC ACA GTT GCT AAG GAT TCT ACT GAA CCA
Arg Val Asn Gly Gly Ile Thr Val Ala Lys Asp Ser Thr Glu Pro
                115             120                 125

CAA CAT GAG GAT ATT AAG ATG GTG ATT AAT AAT
Gln His Glu Asp Ile Lys Met Val Ile Asn Asn
                130             135

TAATCAAGTG AGAGGATTGT TATGAGAATA ATGAGTGGAA TGGAAGACCA
ATCTCATGTC GGTGTGGCCT ATCTCCACCT GTTTGCAGTG CCTTTGTTAA
AATAACACAT TGGGGAATAA TAAAGTGAAA CTATATAGAT TGGTTCAGCA
AATTTTCTGT TCAGTTTTCC TCTCACATGT CAATGTCGAT TTTTTGCCGC
GGATCATACA TGTGCTTGGT ATTCTAATCG ATAGAATTAT GGCTCAAATG
GAGGCAGGGA TTATGAGAGT TTATTCGCAT CTCCGGGTCT TCCAACTTAC
GAATTATAAC AAGATTCAAG GATGCATCTG AAGCCAACT TAACGTCTTA
CATCAAAGGA GCTAGCCGAA GTTTATTCCC AGAGCTAGAG GAAGTTCGCT
GCCATGGTTG ATAGTACAAG TAGAACGACG CATGTATTGC TTCCAGGAAT
CACTTCCAGC TTCTCGACAC CTCCAGTGGC CTTTTCACCA CCGAAAGCAC
CACCAATTTC AGCACCATTG GTAGGTATAT TTACATTAAC AATACCACAG
TCACTGCCAT GGGGTCCAAT CCACTTGAAA ATAACTTCAG GTCTACGAGT
GAAAATAGAA CTGCTTAAAC TTGCGGTACA GAGTTATTTA TTTCAATTGC
TTCTTTCAGA GTCTGGAATT TCATTACGTA AA (SEQ. ID. NO: 3)
```

Example 12

Expression

Figure 4:
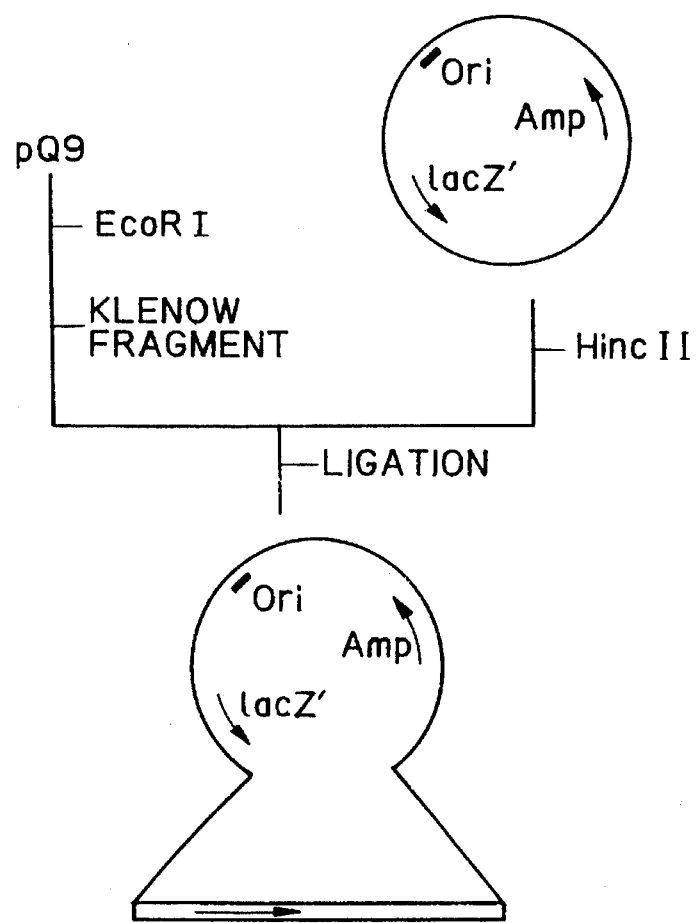
FIG. 4 illustrates the process of preparation and structure of the expression plasmid.

An expression vector was prepared by the method described in the above-mentioned reference of Hanahan et al. Namely, the plasmid pQ9 (10 μg) was digested by EcoRI and then was filled in by Klenow fragments (1.0 μl: 5.0 units) to obtain DNA fragment (about 1.2 kbp) encoding curculin B, then 100 ng of the DNA fragment was inserted into pUC18 (50 ng) digested by HincII to prepare a recombinant plasmid (see FIG. 4). On the other hand, the E. coli YA21 strain was made competent by the calcium method, and transformation was carried out by the above-mentioned recombinant plasmid. The transformants were inoculated in 0.2 ml of χ-broth medium containing 50 μg/ml of ampillicin and incubated at 37° C. for 18 hours. Then, the bacterial suspension was centrifuged (10 minutes at 3000×g), about 5 μg of the resulting precipitate was suspended in 1.0 ml of M9 medium and preliminarily incubated. Thereafter, isopropyl-β-D-thiogalactopyranoside (IPTG) was added at a concentration of 1 mM and incubation was continued for further two hours.

Example 13

Preparation of Antiserum

A 0.1M PBS phosphate physiological buffer solution (pH 7.6) including 1 mg/4 ml of curculin A prepared in Reference Example 4 (vide infra) and identified in Reference Example 5 (vide infra) was used as an antigen solution (for one immunization). The water-in-oil emulsions obtained by mixing 4 ml of the antigen solution with equal amounts of Freund's complete adjuvant (FCA) or Freund's incomplete adjuvant (FIA) were used as the FCA antigen solution and the FIA antigen solution, respectively. Two ml of the above-mentioned FCA antigen solution were injected intramuscularly into the left and right thighs of rabbits (two females of about 1.5 kg body weight) to immunize the same (initial immunization). After one week elapsed from the initial immunization, immunization was carried out (additional immunization) in the same manner as the initial immunization except for the use of the FIA antigen solution. After one week elapsed from the additional immunization, 30 ml/rabbit of blood was sampled. The obtained blood was allowed to stand at room temperature for about 2 hours, then was centrifuged at 3500 rpm for 5 minutes. The supernatant was further centrifuged at 10,000 rpm for 20 minutes, and antiserum containing anti-curculin A antibodies was prepared from the supernatant. The antiserum was treated by column chromatography (column 1.0×4.0 cm, natural falling) using insoluble protein A so as to prepare the purified antiserum.

Example 14

Western Analysis

Figure 5:
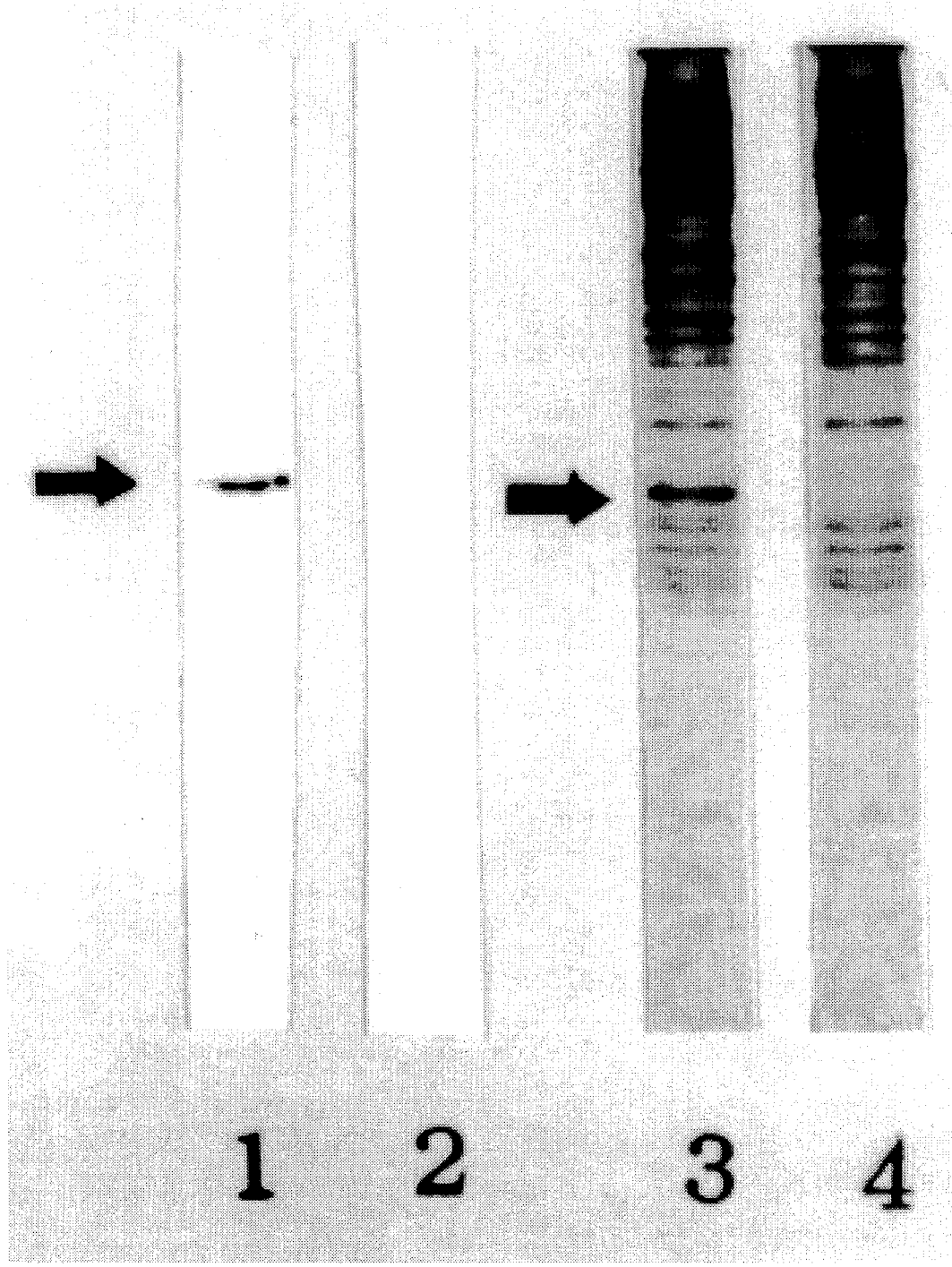
FIG. 5 illustrates the results of electrophoresis and Western analysis.

The cells obtained in Example 12 were suspended in 100 μl of a 10 mM tris-1 mM-EDTA buffer solution (pH 7.5) containing 1 mM-PMSF (phenylmethanesulfonylfluoride), and destroyed by ultrasonication. Then, 3 μl of the resulting liquid was separated by SDS-polyacrylamide gel electrophoresis. The results are shown in lane 3 of FIG. 5. Lane 4 of FIG. 5 is a control lane and was obtained by destroying the E. coli YA21 strain transformed by a plasmid without the recombination procedure of Example 12 and separating the resulting liquid by SDS-polyacrylamide gel electrophoresis in the same manner as above. As shown by the arrow mark at the left of lane 3, a protein component is found at the position of about 17 kd. As markers (not shown), Pre-stained SDS-PAGE Standards (containing phosphorylase B (110 kd), bovine serum albumin (84 kd), ovalbumin (47 kd), carbonic anhydrase (33 kd), soybean trypsin inhibitor (24 kd), and lysozyme (16 kd); Biorad Laboratories) was used.

Then, the separated component was transferred to a nitrocellulose membrane filter. The membrane filter was washed at room temperature for 5 minutes with a 10 mM sodium phosphate buffer solution (pH 7.4; containing 0.14M sodium chloride and 0.05% (v/v) Twin 20; hereinafter referred to as TPBS), then a 20 mM sodium phosphate buffer solution (pH 7.4; containing 3% albumin and 0.5M sodium chloride) was added as a blocking solution. The mixture was allowed to stand at 37° C. for 60 minutes, whereby blocking was carried out. The purified antiserum obtained in Example 13 was diluted to 1500 volumes, 10 ml of the 1500-dilution purified antiserumwas added to the above-mentioned membrane filter. The filter was allowed to stand at 4° C. for one day. After washing with TPBS three times, a secondary antibody was added. Then, the filter was allowed to stand at room temperature for 2 hours. As the secondary antibody, 5 ml of a 1000-dilution of alkali-phosphatase conjugate anti-rabbit IgG (Sigma Co.) was used.

Subsequently, about 10 ml of alkali-phosphatase buffer solution was added, the filter was allowed to stand at room temperature for 10 minutes. Then, a substrate solution comprising 66 μl of an NBT (nitro blue tetrazorium) solution 33 μl of a BCIP (5-bromo-4-chloro-3-indolylphosphate) solution, and 9.9 ml of an alkaliphosphatase buffer solution were added, the filter was allowed to develop color at room temperature for 5 minutes. The reaction was stopped by adding a 3% trichloroacetic acid solution, and the filter was rinsed with distilled water. The NBT solution was prepared by dissolving 50 mg of NBT in 1 ml of 70% dimethylformamide, and the BCIP solution was prepared by dissolving 50 mg of BCIP in 1 ml 100% formamide.

The results are shown by lane 1 and lane 2 in FIG. 5. Lane 1 is a transfer of lane 3, while lane 2 is a transfer of lane 4 (for control). Lane 2 does not include any component reacting with the anti-curculin A antibody, while lane 1, as shown by the arrow mark to the left side, includes the component which reacts with the anti-curculin A antibody at a position corresponding to the protein appearing at the position of about 17 kd of lane 3.

Reference Example 1

Rinsing and Extraction by Sodium Chloride Solution

About 30 g of the pulp of Curculigo latifolia was taken, and 40 ml of water was added thereto. The mixture was homogenized and centrifuged (12,500 rpm, 60 minutes). The supernatant displayed a brown color and did not have a taste-modifying activity. To the resulting residue, 40 ml of water was added, and the mixture was homogenized and centrifuged (12,500 rpm, 20 minutes). The supernatant was colorless and did not have a taste-modifying activity.

Then, an aqueous solution of 0.5M sodium chloride was added to the resulting residue. The mixture was homogenized and centrifuged (30,000 rpm, 60 minutes). The resulting supernatant was colorless and displayed a taste-modifying activity. The extraction procedure was repeated three times using 40 ml of an aqueous solution of 0.5M sodium chloride, then the three supernatants were combined to obtain a crude extract containing curculin.

Reference Example 2

Salting-out by Ammonium Sulfate

To the crude extract obtained in Reference Example 1, ammonium sulfate was added to a 80% saturation so as to precipitate the active substance. The resulting liquid was centrifuged (32,000 rpm, 60 minutes) to obtain the precipitate, which was then dissolved in 100 ml of a 0.01M phosphate buffer solution (pH 6.8).

Reference Example 3

CM-Sepharose Ion Exchange Chromatography

Figure 6:
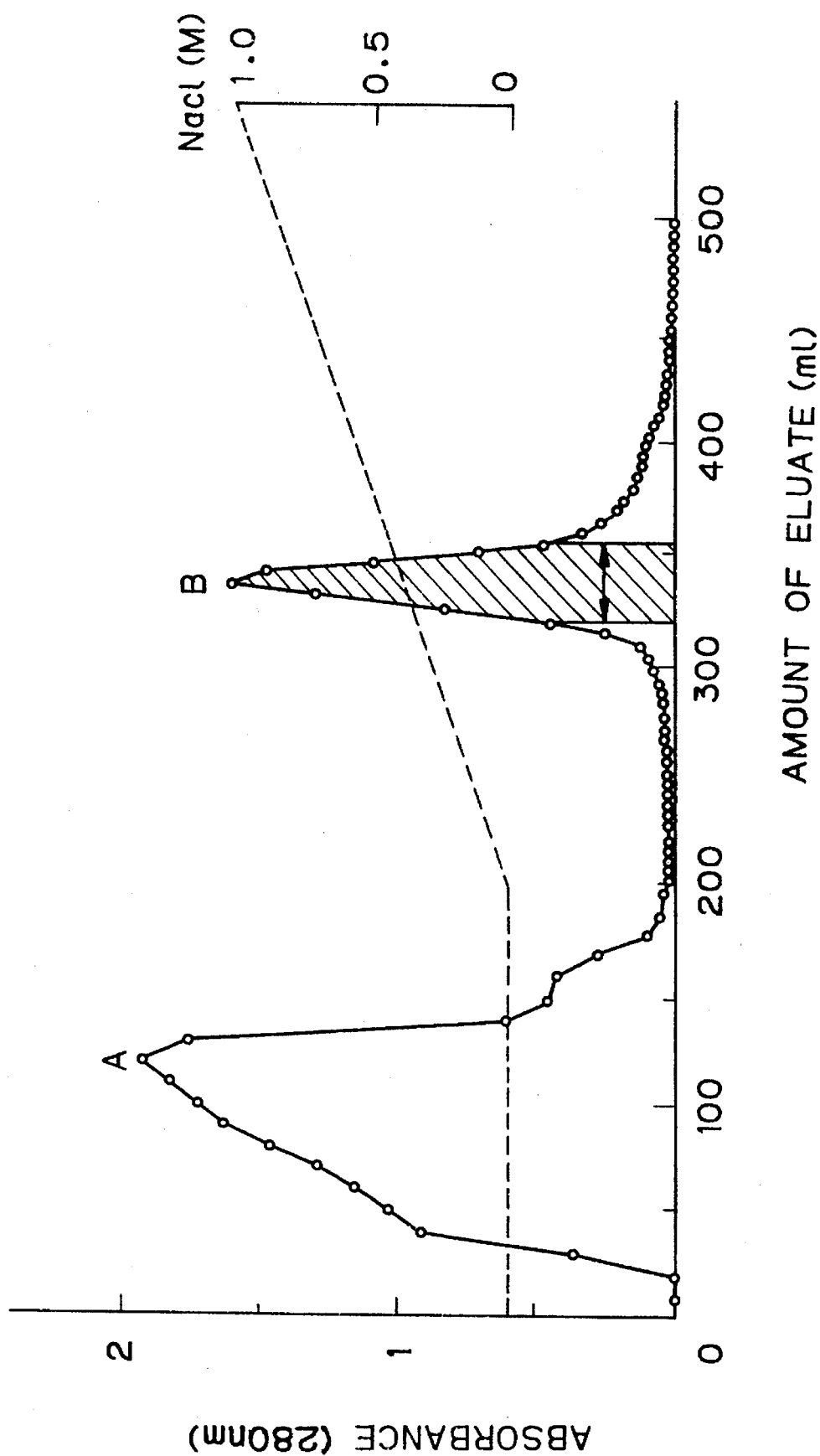
FIG. 6 is a graph showing the elution pattern of CM-sepharose ion exchange chromatography of a taste modifier obtained by a rinsing, extraction and desalting procedure from the fruit of *Curculigo latifolia*.

The solution obtained in Reference Example 2 was passed through a CM-Sepharose CL-6B column (diameter=2.2×18 cm; bed volume=68 ml; Pharmacia LKB Biotechnology Co.) for adsorption. Thereafter, the unabsorbed fraction was removed by a 0.01M phosphate buffer solution (pH 6.8), and then the curculin was eluted by linear gradient elution with 0 to 1.0M sodium chloride solution (flow rate=5 ml/hour; one fraction=5 ml; total eluent=500 ml). The eluted protein was monitored by the absorption at 280 run. The results are shown in FIG. 6. The peak (B) shown in FIG. 6 is the fraction including the taste-modifier curculin.

Reference Example 4

Molecular Sieve Chromatography

To the fraction shown by the hatched portion of the peak (B) of FIG. 6, obtained in Reference Example 3, ammonium sulfate was added until 80% saturation so as to precipitate the active substance. The resulting liquid was centrifuged (32,000 rpm, 60 minutes) to obtain a precipitate, which was then dissolved in 1.5 ml of a 0.01M phosphate buffer solution (pH 6.8). The resulting concentrated solution was separated using a Sephadex (Pharmacia LKB Biotechnology Co.) G-100 column (diameter=1.6 cm×58 cm; bed volume=160 ml) and a 0.01M phosphate buffer solution (pH 6.8) including 0.5 M-NaCl (flow rate=8.4 ml/hour; one fraction=2.8 ml; total eluent=182 ml). The protein was monitored by the absorption at 280 nm. The peak (A) shown in FIG. 7 is the fraction including the taste-modifier curculin.

Reference Example 5

SDS-Polyacrylamide Gel Electrophoresis

Figure 7:
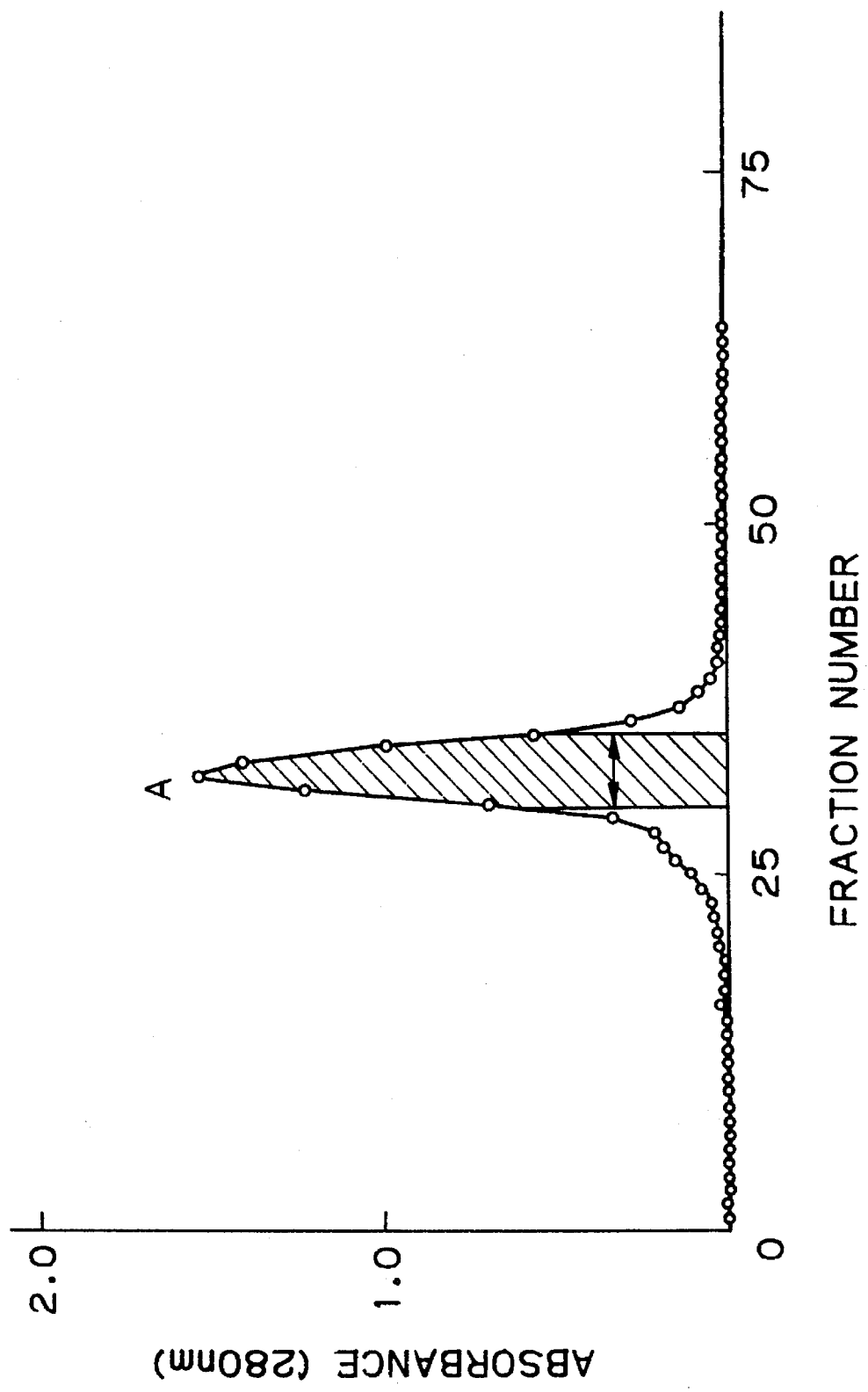
FIG. 7 is a graph showing the elution pattern of Sephadix G-100 molecular sieve chromatography of the fraction shown by the hatching of the peak (B) of FIG. 6.

The purity and the molecular weight of the substance of the fraction shown by the hatched portion of the peak (A) of FIG. 7, obtained in Reference Example 4, were determined by SDS-polyacrylamide gel electrophoresis containing 8M urea. As a result, a single band was shown at a molecular weight of 12,000 daltons, so it was confirmed that the taste-modifier curculin of the fraction shown by the hatched portion of the peak (A) of FIG. 7 was pure. Accordingly, the resulting purified curculin was named "curculin in A".

The content of protein, the yield of the active substance, and the degree of purification of the curculin fractions obtained from 30 g of *Curculigo latifolia* pulp were shown in Table 2. The protein content was determined by the method of Lowry et al.

Figure 8:
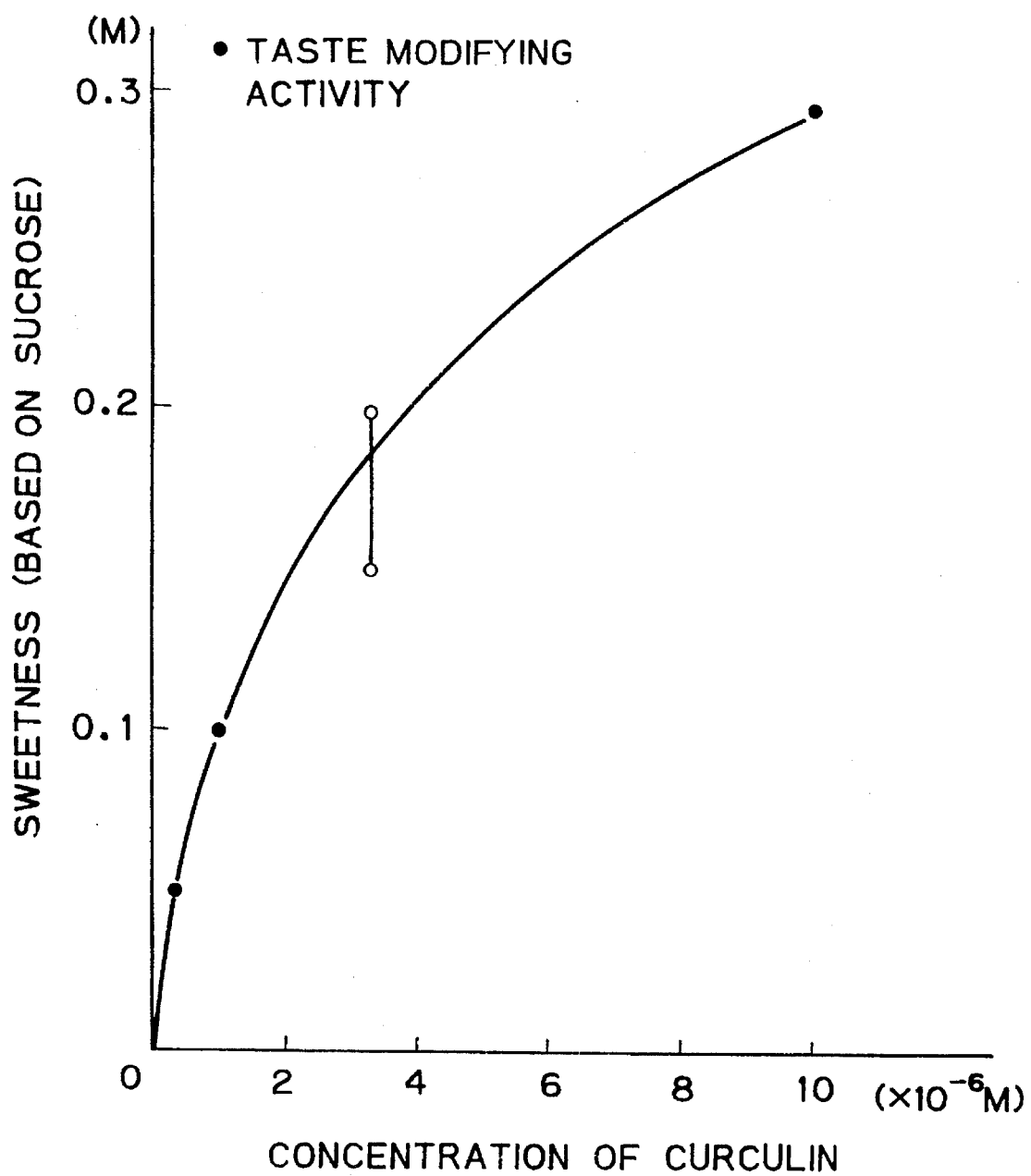
FIG. 8 is a graph showing the activity of a taste-modifier comprised of high purity curculin A.

Further, the activity was measured by keeping a sample in the mouth for 3 minutes, and rinsing the mouth out with water. Then, the sweetness was compared upon tasting a 0.02M citric acid solution with sucrose solutions having various concentrations so as to find the sucrose concentration giving the equivalent sweetness. The results are shown in FIG. 8. As will be understood from FIG. 8, the activity of high purity curculin A corresponded to the sweetness of 0.3M sucrose.

TABLE 2

| Purifying stages | Protein content (g) | Yield of active substance (%) | Purification degree (times) |
|---|---|---|---|
| Pulp | 30*[1] | 100 | 1 |
| Extraction with 0.5M-NaCl aqueous solution | 0.106 | 80.0 | 225 |
| Fraction eluted through CM-Sepharose | 0.018 | 55.5 | 940 |
| Fraction eluted through Sephadex G-100 | 0.0086 | 36.0 | 1255 |

*[1]Pulp weight (including components other than proteins)

Reference Example 6

Isoelectric Point Electrophoresis

Isoelectric point electrophoresis of the high purity curculin A was carried out by the PhastSystem (trademark) (Pharmacia LKB Biotechnology Co.) using PhastGel IEF5-8, whereupon the isoelectric point was found to be 7.1.

In accordance with the present invention, essentially pure and stable curculin B can be prepared by the procedure easier than the prior art and mass production thereof is possible.

Although the present invention has been described with reference to specific embodiments, various changes and modifications obvious to those skilled in the art are deemed to be within the spirit, scope and concept of the invention.

---

We claim:

1. A purified DNA molecule comprising a base sequence encoding a polypeptide of an amino acid sequence of the formula (I):

Asp Asn Val Leu Leu Ser Gly Gln Thr Leu His Ala Asp His Ser
Leu Gln Ala Gly Ala Tyr Thr Leu Thr Ile Gln Asn Lys Cys Asn
Leu Val Lys Tyr Gln Asn Gly Arg Gln Ile Trp Ala Ser Asn Thr
Asp Arg Arg Gly Ser Gly Cys Arg Leu Thr Leu Leu Ser Asp Gly
Asn Leu Val Ile Tyr Asp His Asn Asn Asn Asp Val Trp Gly Ser
Ala Cys Trp Gly Asp Asn Gly Lys Tyr Ala Leu Val Leu Gln Lys
Asp Gly Arg Phe Val Ile Tyr Gly Pro Val Leu Trp Ser Leu Gly
Pro Asn Gly Cys Arg Arg Val Asn Gly    (I). SEQ ID. NO. 1

2. A purified DNA molecule comprising a base sequence encoding a polypeptide of an amino acid sequence of the formula (II):

| Met | Ala | Ala | Lys | Phe | Leu | Leu | Thr | Ile | Leu | Val | Thr | Phe | Ala | Ala |
| Val | Ala | Ser | Leu | Gly | Met | Ala | Asp | Asn | Val | Leu | Leu | Ser | Gly | Gln |
| Thr | Leu | His | Ala | Asp | His | Ser | Leu | Gln | Ala | Gly | Ala | Tyr | Thr | Leu |
| Thr | Ile | Gln | Asn | Lys | Cys | Asn | Leu | Val | Lys | Tyr | Gln | Asn | Gly | Arg |
| Gln | Ile | Trp | Ala | Ser | Asn | Thr | Asp | Arg | Arg | Gly | Ser | Gly | Cys | Arg |
| Leu | Thr | Leu | Leu | Ser | Asp | Gly | Asn | Leu | Val | Ile | Tyr | Asp | His | Asn |
| Asn | Asn | Asp | Val | Trp | Gly | Ser | Ala | Cys | Trp | Gly | Asp | Asn | Gly | Lys |
| Tyr | Ala | Leu | Val | Leu | Gln | Lys | Asp | Gly | Arg | Phe | Val | Ile | Tyr | Gly |
| Pro | Val | Leu | Trp | Ser | Leu | Gly | Pro | Asn | Gly | Cys | Arg | Arg | Val | Asn |
| Gly | Gly | Ile | Thr | Val | Ala | Lys | Asp | Ser | Thr | Glu | Pro | Gln | His | Glu |
| Asp | Ile | Lys | Met | Val | Ile | Asn | Asn | (II) seq ID No. 2. | | | | | | |

3. A purified DNA molecule comprising a base sequence of the formula (IV):

| GAC | AAT | GTC | CTG | CTC | TCC | GGG | CAA | ACT | CTG | CAT | GCC | GAC | CAC | TCT |
| CTC | CAG | GCG | GGC | GCC | TAT | ACC | TTA | ACC | ATA | CAA | AAC | AAG | TGC | AAC |
| CTG | GTG | AAA | TAC | CAG | AAC | GGG | AGG | CAG | ATC | TGG | GCT | AGC | AAC | ACT |
| GAC | AGG | CGG | GGC | TCC | GGC | TGC | CGC | CTC | ACA | TTG | CTG | AGT | GAC | GGG |
| AAC | CTC | GTT | ATC | TAC | GAC | CAC | AAC | AAC | AAC | GAC | GTG | TGG | GGG | AGC |
| GCC | TGC | TGG | GGG | GAC | AAC | GGC | AAG | TAT | GCT | CTT | GTT | CTT | CAG | AAG |
| GAT | GGC | AGA | TTT | GTC | ATC | TAT | GGC | CCG | GTT | TTG | TGG | TCC | CTT | GGC |
| CCT | AAT | GGG | TGC | CGC | CGT | GTT | AAT | GGT | (SEQ ID NO: 4) | | | | | |

4. A purified DNA molecule comprising a base sequence of the formula (V):

| ATG | GCG | GCC | AAG | TTT | CTT | CTC | ACC | ATT | CTT | GTC | ACC | TTT | GCG | GCC |
| GTC | GCT | AGC | CTT | GGC | ATG | GCC | GAC | AAT | GTC | CTG | CTC | TCC | GGG | CAA |
| ACT | CTG | CAT | GCC | GAC | CAC | TCT | CTC | CAG | GCG | GGC | GCC | TAT | ACC | TTA |
| ACC | ATA | CAA | AAC | AAG | TGC | AAC | CTG | GTG | AAA | TAC | CAG | AAC | GGG | AGG |
| CAG | ATC | TGG | GCT | AGC | AAC | ACT | GAC | AGG | CGG | GGC | TCC | GGC | TGC | CGC |

| -continued | | | | | | | | | | | | | | |
|---|---|---|---|---|---|---|---|---|---|---|---|---|---|---|
| CTC | ACA | TTG | CTG | AGT | GAC | GGG | AAC | CTC | GTT | ATC | TAC | GAC | CAC | AAC |
| AAC | AAC | GAC | GTG | TGG | GGG | AGC | GCC | TGC | TGG | GGG | GAC | AAC | GGC | AAG |
| TAT | GCT | CTT | GTT | CTT | CAG | AAG | GAT | GGC | AGA | TTT | GTC | ATC | TAT | GGC |
| CCG | GTT | TTG | TGG | TCC | CTT | GGC | CCT | AAT | GGG | TGC | CGC | CGT | GTT | AAT |
| GGT | GGA | ATC | ACA | GTT | GCT | AAG | GAT | TCT | ACT | GAA | CCA | CAA | CAT | GAG |
| GAT | ATT | AAG | ATG | GTG | ATT | AAT | AAT | (SEQ ID NO.: 5). | | | | | | |

5. A process for producing curculin B comprising:

culturing a transformed cell or microorganism containing a recombinant DNA containing the base sequence of SEQ ID No. 4 or SEQ ID No. 5 whereby curculin B is produced by said transformed cell or microorganism, and isolating curculin B from said transformed cell or microorganism.

6. A process for producing a DNA molecule comprising the base sequence encoding curculin B, comprising separating a mRNA fraction containing curculin B mRNA from *Curculigo latifolia*, preparing single-stranded DNA from said mRNA using reverse transcriptase, preparing double-stranded DNA from said single-stranded DNA, inserting said double-stranded DNA into a vector, transforming a host with said vector having the double-stranded DNA inserted therein to produce a cDNA library, and isolating from said library a cDNA having the base sequence of SEQ ID No. 4 or SEQ ID No. 5, using one or more synthesized probes containing a base sequence coding for a partial amino acid sequence elucidated from curculin A purified from *Curculigo latifolia*.

7. A process according to claim 6, wherein the probe is selected from the group consisting of SEQ ID No. 6, SEQ ID No. 7, and SEQ ID No. 8 or combinations thereof.

8. The process according to claim 7, wherein the probe consists of an oligonucleotide having a first segment which consists of the sequence of SEQ ID NO:6 and a second segment which consists of the sequence of either SEQ ID NO:7 or SEQ ID NO:8.

9. A process according to claim 7, wherein the probe consists of an oligonucleotide having a first segment which consists of the sequence of SEQ ID NO:6, a second segment which consists of the sequence of SEQ ID NO:7, and a third segment which consists of the sequence of SEQ ID NO:8.

* * * * *

UNITED STATES PATENT AND TRADEMARK OFFICE
CERTIFICATE OF CORRECTION

PATENT NO. : 5,480,795
DATED : January 2, 1996
INVENTOR(S) : Yoshie Kurihara, Soichi Arai, Keiko Abe and Haruyuki Yamashita It is certified that error appears in the above-indentified patent and that said Letters Patent is hereby corrected as shown below:

Change the address of the second inventor, Soichi Arai, as follows:

Delete "Kanagawa-Ku" and insert --Kanagawa-ku--.

Signed and Sealed this

Ninth Day of July, 1996

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES:9

( 2 ) INFORMATION FOR SEQ ID NO: 1:

( i ) SEQUENCE CHARACTERISTICS:
        ( A ) LENGTH:114 amino acids
        ( B ) TYPE:amino acid
        ( C ) TOPOLOGY:linear ( i i ) MOLECULE TYPE:Peptide ( i i i ) HYPOTHETICAL:no ( v i ) ORIGINAL SOURCE:
        ( A ) ORGANISM:Curculigo latifolia ( i x ) FEATURE:
        ( A ) NAME/KEY:Curculin B
        ( B ) LOCATION:amino acids, 1 to 114
        ( C ) IDENTIFICATION METHOD:Similarity with known sequence of curculin A
        ( D ) OTHER INFORMATION:Useful as a taste modifier ( x i ) SEQUENCE DESCRIPTION:SEQ ID NO:1:

Asp Asn Val Leu Leu Ser Gly Gln Thr Leu His Ala Asp His Ser
1               5                   10                  15

Leu Gln Ala Gly Ala Tyr Thr Leu Thr Ile Gln Asn Lys Cys Asn
                20                  25                  30

```
Leu  Val  Lys  Tyr  Gln  Asn  Gly  Arg  Gln  Ile  Trp  Ala  Ser  Asn  Thr
               35                       40                           45

Asp  Arg  Arg  Gly  Ser  Gly  Cys  Arg  Leu  Thr  Leu  Leu  Ser  Asp  Gly
               50                       55                           60

Asn  Leu  Val  Ile  Tyr  Asp  His  Asn  Asn  Asp  Val  Trp  Gly  Ser
               65                       70                           75

Ala  Cys  Trp  Gly  Asp  Asn  Gly  Lys  Tyr  Ala  Leu  Val  Leu  Gln  Lys
               80                       85                           90

Asp  Gly  Arg  Phe  Val  Ile  Tyr  Gly  Pro  Val  Leu  Trp  Ser  Leu  Gly
               95                      100                          105

Pro  Asn  Gly  Cys  Arg  Arg  Val  Asn  Gly
                        110
```

( 2 ) INFORMATION FOR SEQ ID NO: 2:

( i ) SEQUENCE CHARACTERISTICS:
        ( A ) LENGTH:158 amino acids
        ( B ) TYPE:amino acids
        ( C ) TOPOLOGY:linear ( i i ) MOLECULE TYPE:peptide ( i i i ) HYPOTHETICAL:no ( v i ) ORIGINAL SOURCE:
        ( A ) ORGANISM:Curculigo latifolia ( i x ) FEATURE:
        ( A ) NAME/KEY:Curculin B. Pre- propeptide
        ( B ) LOCATION:–22 to 136
        ( C ) IDENTIFICATION METHOD:similarity with known sequence of
            curculin A ( x i ) SEQUENCE DESCRIPTION:SEQ ID NO: 2:

```
Met  Ala  Ala  Lys  Phe  Leu  Leu  Thr  Ile  Leu  Val  Thr  Phe  Ala  Ala
               20                       15                   10

Val  Ala  Ser  Leu  Gly  Met  Ala  Asp  Asn  Val  Leu  Leu  Ser  Gly  Gln
                5                        1                    5

Thr  Leu  His  Ala  Asp  His  Ser  Leu  Gln  Ala  Gly  Ala  Tyr  Thr  Leu
          10                       15                       20

Thr  Ile  Gln  Asn  Lys  Cys  Asn  Leu  Val  Lys  Tyr  Gln  Asn  Gly  Arg
          25                       30                       35

Gln  Ile  Trp  Ala  Ser  Asn  Thr  Asp  Arg  Arg  Gly  Ser  Gly  Cys  Arg
          40                       45                       50

Leu  Thr  Leu  Leu  Ser  Asp  Gly  Asn  Leu  Val  Ile  Tyr  Asp  His  Asn
          55                       60                       65

Asn  Asn  Asp  Val  Trp  Gly  Ser  Ala  Cys  Trp  Gly  Asp  Asn  Gly  Lys
     70                            75                       80

Tyr  Ala  Leu  Val  Leu  Gln  Lys  Asp  Gly  Arg  Phe  Val  Ile  Tyr  Gly
     85                            90                       95

Pro  Val  Leu  Trp  Ser  Leu  Gly  Pro  Asn  Gly  Cys  Arg  Arg  Val  Asn
     100                          105                       110

Gly  Gly  Ile  Thr  Val  Ala  Lys  Asp  Ser  Thr  Glu  Pro  Gln  His  Glu
     115                          120                       125

Asp  Ile  Lys  Met  Val  Ile  Asn  Asn
     130                          135
```

( 2 ) INFORMATION FOR SEQ ID NO: 3:

( i ) SEQUENCE CHARACTERISTICS:

(A) LENGTH:1166 nucleotides
(B) TYPE:nucleic acid
(C) STRANDEDNESS:double-stranded
(D) TOPOLOGY:linear (ii) MOLECULE TYPE:Genomic DNA (iii) HYPOTHETICAL:no (vi) ORIGINAL SOURCE:
    (A) ORGANISM:Curculigo latifolia (ix) FEATURE:
    (A) NAME/KEY:plasmid pQG
    (B) LOCATION:nucleic acid −76 to 990
    (C) IDENTIFICATION METHOD:Hybridization to oligonucleotides (xi) SEQUENCE DESCRIPTION:SEQ ID NO: 3:

```
CGCAAAGACA ATG GCG GCC AAG TTT CTT CTC ACC ATT CTT GTC ACC        46
TTT GCG GCC GTC GCT AGC TTT GGC ATG GCC GAC AAT GTC CTG CTC        91
TCC GGG CAA ACT CTG CAT GCC GAC CAC TCT CTC CAG GCG GGC GCC       136
TAT ACC TTA ACC ATA CAA AAC AAG TGC AAC CTG GTG AAA TAC CAG       181
AAC GGG AGG CAG ATC TGG GCT AGC AAC ACT GAC AGG CGG GGC TCC       226
GGC TGC CGC CTC ACA TTG CTG AGT GAC GGG AAC CTC GTT ATC TAC       271
GAC CAC AAC AAC AAC GAC GTG TGG GGG AGC GCC TGC TGG GGG GAC       316
AAC GGC AAG TAT GCT CTT GTT CTT CAG AAG GAT GGC AGA TTT GTC       361
ATC TAT GGC CCG GTT TTG TGG TCC CTT GGC CCT AAT GGG TGC CGC       406
CGT GTT AAT GGT GGA ATC ACA GTT GCT AAG GAT TCT ACT GAA CCA       451
CAA CAT GAG GAT ATT AAG ATG GTG ATT AAT AAT                       484
TAATCAAGTG AGAGGATTGT TATGAGAATA ATGAGTGGAA TGGAAGACCA            534
ATCTCATGTC GGTGTGGCCT ATCTCCACCT GTTGCAGTG CCTTTGTTAA             584
AATAACACAT TGGGGAATAA TAAAGTGAAA CTATATAGAT TGGTTCAGCA            634
AATTTTCTGT TCAGTTTTCC TCTCACATGT CAATGTCGAT TTTTTGCCGC            684
GGATCATACA TGTGCTTGGT ATTCTAATCG ATAGAATTAT GGCTCAAATG            734
GAGGCAGGGA TTATGAGAGT TTATTCGCAT CTCCGGGTCT TCCAACTTAC            784
GAATTATAAC AAGATTCAAG GATGCATCTG AGAGCCAACT TAACGTCTTA            834
CATCAAAGGA GCTAGCCGAA GTTTATTCCC AGAGCTAGAG GAAGTTCGCT            884
GCCATGGTTG ATAGTACAAG TAGAACGACG CATGTATTGC TTCCAGGAAT            934
CACTTCCAGC TTCTCGACAC CTCCAGTGGC CTTTTCACCA CCGAAAGCAC            984
CACCAATTTC AGCACCATTG GTAGGTATAT TTACATTAAC AATACCACAG           1034
TCACTGCCAT GGGGTCCAAT CCACTTGAAA ATAACTTCAG GTCTACGAGT           1084
GAAAATAGAA CTGCTTAAAC TTGCGGTACA GAGTTATTTA TTTCAATTGC           1134
TTCTTTCAGA GTCTGGAATT TCATTACGTA AA                              1166
```

(2) INFORMATION FOR SEQ ID NO: 4:

(i) SEQUENCE CHARACTERISTICS:
        (A) LENGTH:342 nucleotides
        (B) TYPE:nucleic acid
        (C) STRANDEDNESS:double stranded
        (D) TOPOLOGY:linear (ii) MOLECULE TYPE:genomic DNA (  i i i  ) HYPOTHETICAL:no (  v i  ) ORIGINAL SOURCE:
  ( A ) ORGANISM:Curculigo latifolia (  i x  ) FEATURE:
  ( A ) NAME/KEY:Curculin B coding region
  ( B ) LOCATION:nucleic acid 1 to 342

(  x i  ) SEQUENCE DESCRIPTION:SEQ ID NO: 4:

| | | | | | | | | | | | | | | |
|---|---|---|---|---|---|---|---|---|---|---|---|---|---|---|
| GAC | AAT | GTC | CTG | CTC | TCC | GGG | CAA | ACT | CTG | CAT | GCC | GAC | CAC | TCT | 45 |
| CTC | CAG | GCG | GGC | GCC | TAT | ACC | TTA | ACC | ATA | CAA | AAC | AAG | TGC | AAC | 90 |
| CTG | GTG | AAA | TAC | CAG | AAC | GGG | AGG | CAG | ATC | TGG | GCT | AGC | AAC | ACT | 135 |
| GAC | AGG | CGG | GGC | TCC | GGC | TGC | CGC | CTC | ACA | TTG | CTG | AGT | GAC | GGG | 180 |
| AAC | CTC | GTT | ATC | TAC | GAC | CAC | AAC | AAC | AAC | GAC | GTG | TGG | GGG | AGC | 225 |
| GCC | TGC | TGG | GGG | GAC | AAC | GGC | AAG | TAT | GCT | CTT | GTT | CTT | CAG | AAG | 270 |
| GAT | GGC | AGA | TTT | GTC | ATC | TAT | GGC | CCG | GTT | TTG | TGG | TCC | CTT | GGC | 315 |
| CCT | AAT | GGG | TGC | CGC | CGT | GTT | AAT | GGT | | | | | | | 342 |

( 2 ) INFORMATION FOR SEQ ID NO: 5:

( i ) SEQUENCE CHARACTERISTICS:
    ( A ) LENGTH:474 nucleotides
    ( B ) TYPE:nucleic acid
    ( C ) STRANDEDNESS:double stranded
    ( D ) TOPOLOGY:linear ( i i ) MOLECULE TYPE:genomic DNA ( i i i ) HYPOTHETICAL:no ( v i ) ORIGINAL SOURCE:
    ( A ) ORGANISM:Curculigo latifolia ( i x ) FEATURE:
    ( A ) NAME/KEY:Curculin B Pre- propeptide coding region
    ( B ) LOCATION:nucleic acid −66 to 409

( x i ) SEQUENCE DESCRIPTION:SEQ ID NO: 5:

| | | | | | | | | | | | | | | |
|---|---|---|---|---|---|---|---|---|---|---|---|---|---|---|
| ATG | GCG | GCC | AAG | TTT | CTT | CTC | ACC | ATT | CTT | GTC | ACC | TTT | GCG | GCC | 45 |
| GTC | GCT | AGC | TTG | GCA | TGG | CCG | ACA | ATG | TCG | TCG | CTC | TCC | GGG | CAA | 90 |
| ACT | CTG | CAT | GCC | GAC | CAC | TCT | CTC | CAG | GCG | GGC | GCC | TAT | ACC | TTA | 135 |
| ACC | ATA | CAA | AAC | AAG | TGC | AAC | CTG | GTG | AAA | TAC | CAG | AAC | GGG | AGG | 180 |
| CAG | ATC | TGG | GCT | AGC | AAC | ACT | GAC | AGG | CGG | GGC | TCC | GGC | TGC | CGC | 225 |
| CTC | ACA | TTG | CTG | AGT | GAC | GGG | AAC | CTC | GTT | ATC | TAC | GAC | CAC | AAC | 270 |
| AAC | AAC | GAC | GTG | TGG | GGG | AGC | GCC | TGC | TGG | GGG | GAC | AAC | GGC | AAG | 315 |
| TAT | GCT | CTT | GTT | CTT | CAG | AAG | GAT | GGC | AGA | TTT | GTC | ATC | TAT | GGC | 360 |
| CCG | GTT | TTG | TGG | TCC | CTT | GGC | CCT | AAT | GGG | TGC | CGC | CGT | GTT | AAT | 405 |
| GGT | GGA | ATC | ACA | GTT | GCT | AAG | GAT | TCT | ACT | GAA | CCA | CAA | CAT | GAG | 450 |
| GAT | ATT | AAG | ATG | GTG | ATT | AAT | AAT | | | | | | | | 474 |

( 2 ) INFORMATION FOR SEQ ID NO: 6:

( i ) SEQUENCE CHARACTERISTICS:
    ( A ) LENGTH:17 nucleotides
    ( B ) TYPE:nucleic acid
    ( C ) STRANDEDNESS:double stranded ( D ) TOPOLOGY:linear ( i i ) MOLECULE TYPE:other nucleic acid; oligonucleotide ( i x ) FEATURE:
            ( A ) NAME/KEY:degenerate oligonucleotide 1
            ( B ) LOCATION:73 to 90
            ( C ) OTHER INFORMATION:
N in the sequence indicates deoxyribonucleic acid residues of A,
C, G or T; H indicates deoxyribonucleic acid residues of A, C or
T; D indicates deoxyribonucleic acid residues of A, G or T; R
indicates deoxyribonucleic acid residues of A or G; K indicates
deoxyribonucleic acid residues of G or T; and Y indicates
deoxyribonucleic acid residues of C or T.

( x i ) SEQUENCE DESCRIPTION:SEQ ID NO: 6:

ATHCARAAKA AKTGYAA                                                                          17

( 2 ) INFORMATION FOR SEQ ID NO: 7:

( i ) SEQUENCE CHARACTERISTICS:
            ( A ) LENGTH:26 nucleotides
            ( B ) TYPE:nucleic acid
            ( C ) STRANDEDNESS:double stranded
            ( D ) TOPOLOGY:linear ( i i ) MOLECULE TYPE:other nucleic acid; antisense oligonucleotide ( i x ) FEATURE:
            ( A ) NAME/KEY:degenerate oligonucleotide 2
            ( B ) LOCATION:102 to 126
            ( C ) OTHER INFORMATION:
N in the sequence indicates deoxyribonucleic acid residues of A,
C, G or T; H indicates deoxyribonucleic acid residues of A, C or
T; D indicates deoxyribonucleic acid residues of A, G or T; R
indicates deoxyribonucleic acid residues of A or G; K indicates
deoxyribonucleic acid residues of G or T; and Y indicates
deoxyribonucleic acid residues of C or T.

( x i ) SEQUENCE DESCRIPTION:SEQ ID NO: 7:

GCCCADATYT GNCKNCCRTT YTGRTA                                                                26

( 2 ) INFORMATION FOR SEQ ID NO: 8:

( i ) SEQUENCE CHARACTERISTICS:
            ( A ) LENGTH:20 nucleotides
            ( B ) TYPE:nucleic acid
            ( C ) STRANDEDNESS:double stranded
            ( D ) TOPOLOGY:linear ( i i ) MOLECULE TYPE:other nucleic acid; antisense oligonucleotide ( i x ) FEATURE:
            ( A ) NAME/KEY:degenerate oligonucleotide 3
            ( B ) LOCATION:282 to 300
            ( C ) OTHER INFORMATION:
N in the sequence indicates deoxyribonucleic acid residues of A,
C, G or T; H indicates deoxyribonucleic acid residues of A, C or
T; D indicates deoxyribonucleic acid residues of A, G or T; R
indicates deoxyribonucleic acid residues of A or G; K indicates
deoxyribonucleic acid residues of G or T; and Y indicates
deoxyribonucleic acid residues of C or T.

( x i ) SEQUENCE DESCRIPTION:SEQ ID NO: 8:

ACNGGNCCRT ADATNACRAA                                                                       20

( 2 ) INFORMATION FOR SEQ ID NO: 9:

( i ) SEQUENCE CHARACTERISTICS:
            ( A ) LENGTH:13 nucleotides
            ( B ) TYPE:nucleic acid
            ( C ) STRANDEDNESS:double stranded
            ( D ) TOPOLOGY:linear (i i) MOLECULE TYPE:ECORI adapter (i i i) HYPOTHETICAL:no (i x) FEATURE:
  (A) NAME/KEY:ECORI adapter (x i) SEQUENCE DESCRIPTION:SEQ ID NO: 9:

AATTCGGCACGAG                    13